(12) United States Patent
Eberle et al.

(10) Patent No.: US 6,282,446 B1
(45) Date of Patent: Aug. 28, 2001

(54) AUTOMATIC SHOCK LEAD GAIN ADJUSTER

(75) Inventors: Jason W. Eberle; LeAnne Marie Mackey, both of St. Louis Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/379,987

(22) Filed: Aug. 24, 1999

Related U.S. Application Data

(63) Continuation-in-part of application No. 09/378,359, filed on Aug. 20, 1999.

(51) Int. Cl.$^7$ ..................................... A61N 1/39
(52) U.S. Cl. ................................. 607/5; 607/31
(58) Field of Search .................. 607/5.7, 27, 28, 607/30, 31, 59; 600/510

(56) References Cited

U.S. PATENT DOCUMENTS

| | | |
|---|---|---|
| 4,966,146 | * 10/1990 | Webb et al. ............... 607/31 |
| 5,411,527 | 5/1995 | Alt . |
| 5,476,485 | 12/1995 | Weinberg et al. . |
| 5,534,018 | 7/1996 | Wahlstrand et al. . |
| 5,620,466 | 4/1997 | Haefner et al. . |
| 5,658,317 | 8/1997 | Haefner et al. . |
| 5,662,688 | 9/1997 | Haefner et al. . |
| 5,690,683 | 11/1997 | Haefner et al. . |
| 5,730,720 | 3/1998 | Sites et al. . |
| 5,755,738 | 5/1998 | Kim et al. . |
| 5,755,742 | 5/1998 | Schuelke et al. . |
| 5,772,692 | 6/1998 | Armstrong . |
| 5,782,876 | 7/1998 | Flammang . |
| 5,814,079 | 9/1998 | Kieval . |
| 5,817,130 | 10/1998 | Cox et al. . |
| 5,954,753 | 9/1999 | Alt et al. . |

FOREIGN PATENT DOCUMENTS

| | | | |
|---|---|---|---|
| 00/24458 | 5/2000 | (WO) | ............... A61N/1/37 |

* cited by examiner

Primary Examiner—George R. Evanisko
(74) Attorney, Agent, or Firm—Schwegman, Lundberg, Woessner & Kluth, P.A.

(57) ABSTRACT

A system and method for automatically adjusting the gain for a shock lead system in an implantable medical device is provided. The system and method operate when, after a pre-selected period of time, the gain has not been programmed. The system and method then automatically produce and set the gain for the shock lead system. The system and method poll and determine a maximum value for the output of the shock lead system amplifier and produce a new gain value to scale the output to facilitate providing useful data that is large enough to separate signal from noise but small enough to avoid clipping.

7 Claims, 9 Drawing Sheets

AUTOMATIC SHOCK LEAD GAIN ADJUSTER

CROSS REFERENCE TO RELATED APPLICATIONS

This application is a continuation-in-part of U.S. Pat. Application No. 09/378,359, filed on Aug. 20, 1999, the specification of which is incorporated herein by reference.

Field of the Invention

The present invention is related to implantable medical devices, and more particularly to a device and method for automatically adjusting the gain for shock leads.

Background Information

Electric shock defibrillation is a proven technique for treatment of the serious and immediately life-threatening condition of ventricular fibrillation. For patients known to be at risk, an implantable defibrillator may be used. Such devices contain an energy source, an electrode lead system in contact in the heart, a sensing system to detect the onset of fibrillation, and a pulse generator for delivering the defibrillation shock.

The electrode lead system may include electrodes to reverse certain life-threatening arrhythmias, like ventricle fibrillation, where electrical energy is applied to the heart via the electrodes to return the heart to normal rhythm. One type of electrode which may be used is a shock lead. In determining when stimulation is needed, a shock lead system senses activity in the heart through a sensing system, e.g. an electrogram channel. To ensure accurate sensing, the shock lead system's electrogram channel must be properly calibrated to provide a set of values for the heart activity within a preset range.

One method for calibrating a shock lead system is to use a programmer device to determine and set a gain value for the shock electrogram channel. The programmer device, external to the patient, collects real-time electrogram data for a period of time and determines the shock channel gain based on amplitudes obtained while collecting data. This method of gain production is susceptible to errors since real-time electrogram data has no error correction, e.g. CRCs, and can be corrupted by noise signals which are prevalent in hospital rooms, the likely programming environment.

Additionally, it is possible that the shock lead system is not properly calibrated after insertion. This can occur if the device is not properly programmed after insertion or if the device is not calibrated at all. The device may not be calibrated at all if a physician fails to program the device after insertion. If the device is not properly calibrated after insertion it will only have a default gain level that is set prior to implantation of the device. With a default gain level, the output signal from the electrogram may be so low that only a flat line is output and the data is not useful for therapeutic purposes. It is also possible that with bad lead placement the signal coming out would be too large resulting in a clipped signal, again making the data useless therapeutic purposes. In either case, the inserted device will not record electrograms properly until programmed manually by a physician. This change may not occur until a patient returns to the doctor or hospital for examination and, in the meantime, valuable therapeutic data will have been lost.

Thus, what is needed in the art is a method and device for automatically calibrating a shock lead system that ensures signal levels are within a prescribed range for the proper functioning of the implantable medical device.

SUMMARY OF THE INVENTION

The present invention provides a system and method for automatically adjusting the gain for a shock lead system in an implantable medical device. According to one aspect of the present invention, the system and method operate when, after a pre-selected period of time, the gain has not been programmed. The system and method automatically determine and set the gain for the shock lead system. The amplifier for the shock lead system is polled to determine a maximum value for the output of the shock lead system amplifier and a new gain value is produced to scale the output to provide useful data. The new gain value facilitates an output of the amplifier that is big enough to not be affected by noise and small enough to avoid clipping.

According to another aspect of the present invention, an implantable medical device includes a shock lead system with at least one shock lead. The implantable medical device also includes an automatic gain adjuster system connected to a shock lead system. The automatic gain adjuster system includes a detector which detects when a gain value for the shock lead system was not set on exiting storage mode. The automatic gain adjuster system also includes a gain determining module which produces and stores a new gain value.

According to yet another aspect of the present invention, it is determined if the gain of a shock lead system for an implantable medical device was programmed within a first period of time. An amplifier for the shock lead system is then enabled and set to a predetermined initial gain value. The amplifier output is then allowed to stabilize. After the amplifier stabilizes, a data storage is cleared of all old values. Data is then collected in the data storage from the output of the amplifier for a designated period of time. Based on the stored data, a peak value for the amplifier output is determined and a new gain value is produced based on the determined peak value. The new gain value is then used to set the gain of the amplifier.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
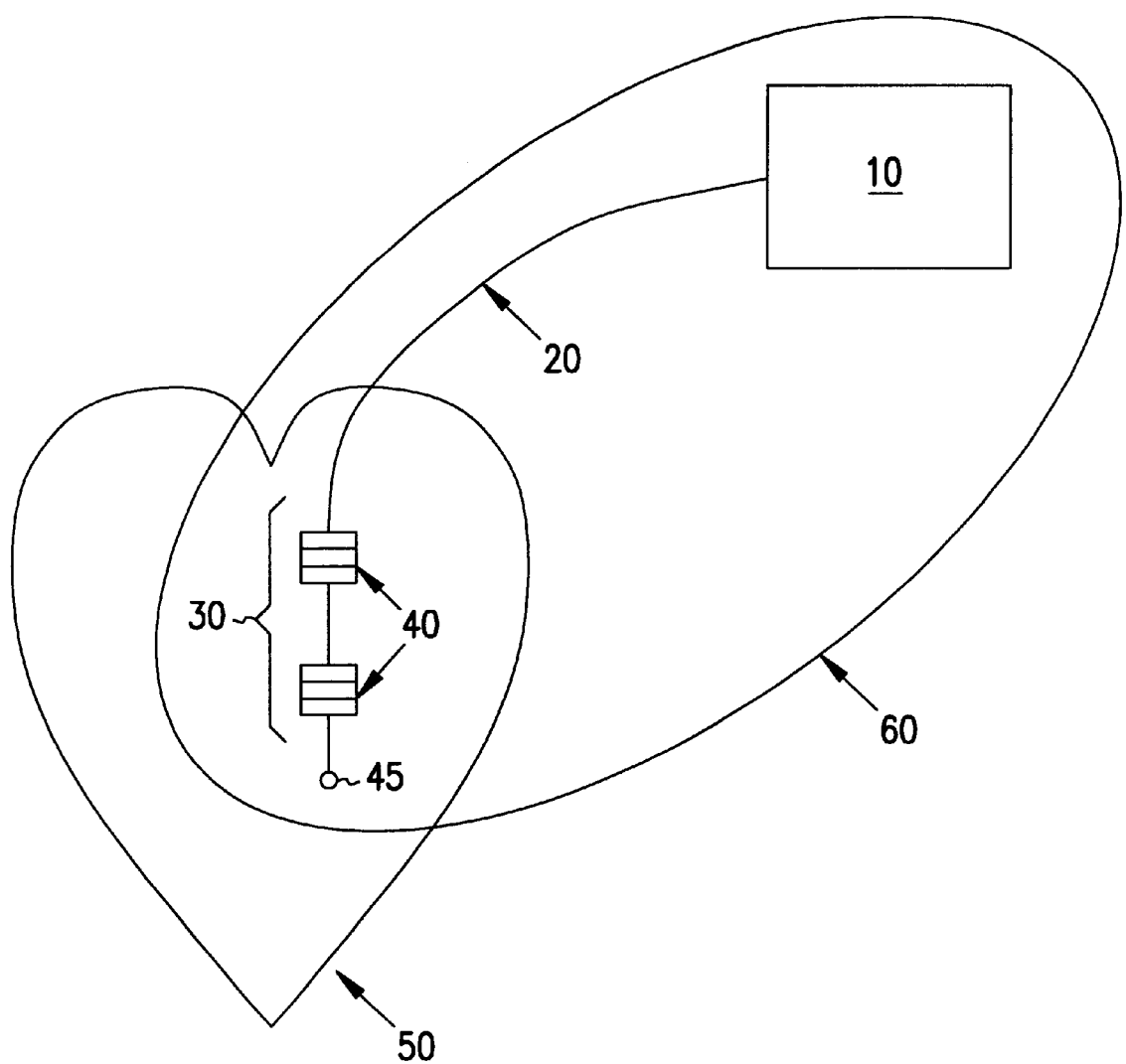
FIG. 1 is a drawing showing one embodiment of an implantable medical system having an automatic gain adjuster according to the present invention.

FIG. 1 illustrates one embodiment of the present invention where shock leads 40, as part of implantable medical system 60, are attached in heart 50. Shown in FIG. 1 is implantable medical system 60 having implantable medical device 10, shock lead system 30 and wires 20, and heart 50. In one embodiment, implantable medical system 60 is an implantable pacing/defibrillator system 60. In another embodiment, the implantable medical system 60 is an implantable defibrillator 60. Shock lead system 30 includes shock leads 40, and in one embodiment, shown in FIG. 1, pacing lead 45, and is coupled to implantable medical device 10 using wires 20. Shock lead system 30 is attached to, or placed in, heart 50 by attaching shock leads 40 to, or inserting shock leads 40 in, heart 50. In one embodiment, pacing lead 45 is also attached to, or placed in, heart 50.

The process of implanting implantable medical system 60 into a patient includes the following steps. First, checking the equipment to include interrogating and checking the pulse generator's nominal settings and battery capacity. Next, the physician implants shock lead system 30, where shock leads 40 are attached to, or placed in, heart 50 through a surgical approach chosen by the physician. Types of surgical approaches are known to those of skill in the art and, therefore, are not described here. Baseline measurements are then taken by the physician using a pacing system analyzer (PSA) to evaluate shock lead system 30 signal amplitude and defibrillation threshold. If baseline measurements are unsatisfactory, shock lead system 30 may need to be repositioned or replaced, as required. Next, the physician forms the implantation pocket. The implantation pocket is formed using standard operating procedures know to those of skill in the art, taking into consideration factors like body habitus, pulse generator size, lead configuration and the patients anatomy. In one embodiment, the pocket is formed in subcutaneous tissue to facilitate magnet application and telemetry between the implantable medical device 10 and a programmer device. In another embodiment, a deeper implantation is used, e.g. subpectoral, to help avoid erosion or extrusion in some patients. The physician then verifies magnet function and telemetry to ensure implantable medical device 10 is within an acceptable range, connects shock lead system 30 to implantable medical device 10 and positions implantable medical device 10 in the implantation pocket. Next, the physician evaluates shock lead system 30 signals using a programmer device to ensure the signals are continuous and without artifact, e.g. similar to a body-surface echocardiogram (ECG). The physician then tests for the ability to convert ventricular fibrillation and inducible arrhythmias using implantable medical device 10 and a programmer device followed by implantation of implantable medical device 10. At this point implantable medical system 60 is properly implanted in the patient.

Figure 2:
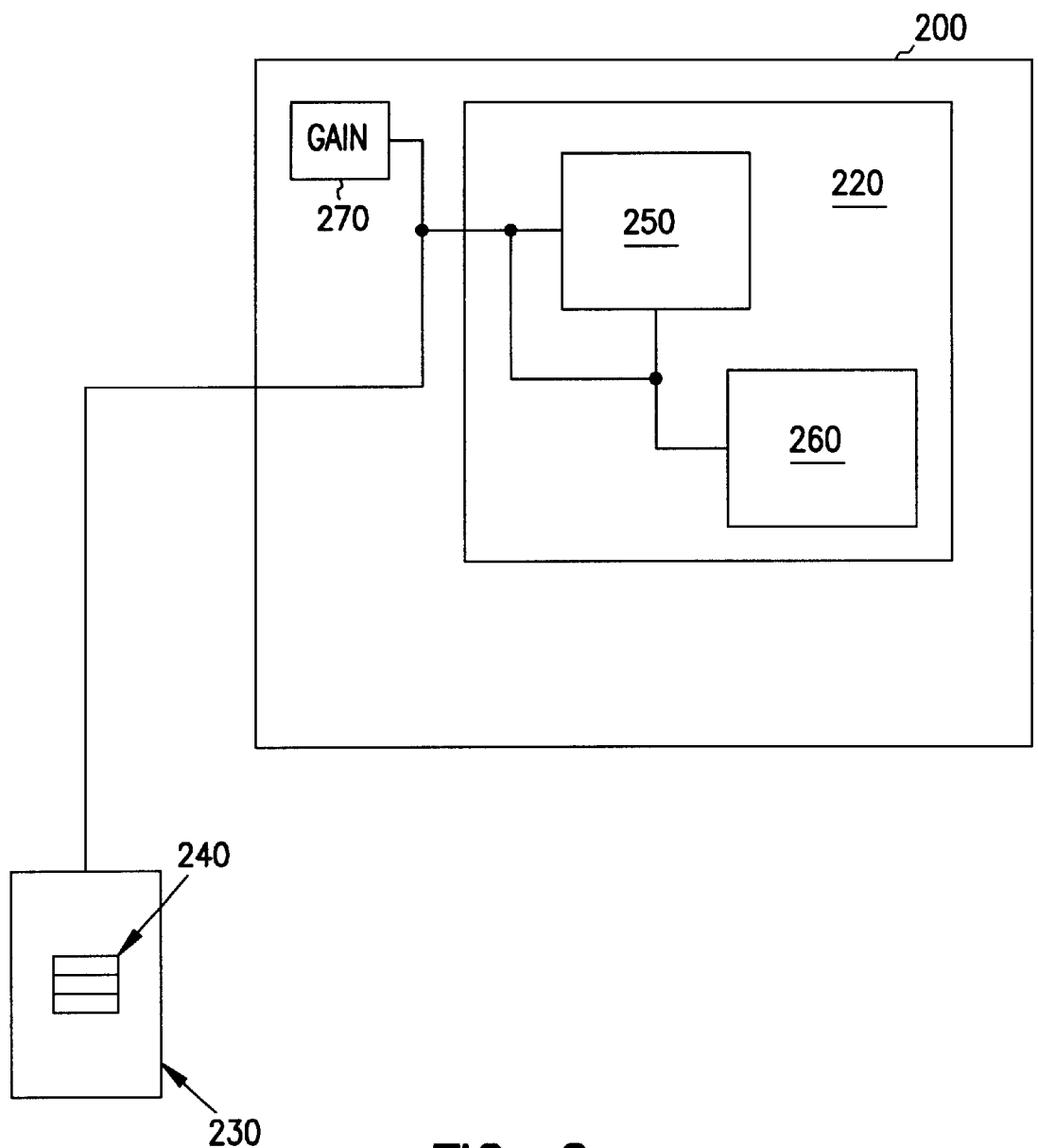
FIG. 2 is a drawing showing one embodiment of a functional diagram of an implantable medical device according to the teachings of the present invention.

FIG. 2 illustrates one embodiment of implantable medical device 200. Additionally, shown in FIG. 2 are shock lead system 230, automatic gain adjusting system 220 and gain 270. In one embodiment, shown in FIG. 2, shock lead system 230 includes shock lead 240. In another embodiment, shock lead system 230 includes a plurality of shock leads 240 and at least one pacing lead. Automatic gain adjusting system 220 includes detector 250 and gain determining module 260. Shock lead system 230 is coupled to implantable medical device 200. Detector 250 is coupled to gain determining module 260 and gain 270. Gain determining module 260 is coupled to shock lead system 230, detector 250 and gain 270.

Implantable medical device 200, shown in FIG. 2, has detector 250 detect when gain 270 for shock lead system 230 was not set on exiting the storage mode for implantable medical device 200. Gain determining module 260 then produces and stores a new gain into gain 270. In one embodiment, gain determining module 260 produces new gain 270 based on a predetermined scaling percentage. In one embodiment, the new value in gain 270 is such that shock lead system 230 operates with an output in a range where values are big enough to separate signal from noise and small enough to avoid clipping. In another embodiment, the new value of gain 270 is determined such that there is an increased probability of producing an output in a range where values are big enough to separate signal from noise and small enough to avoid clipping.

Figure 3:
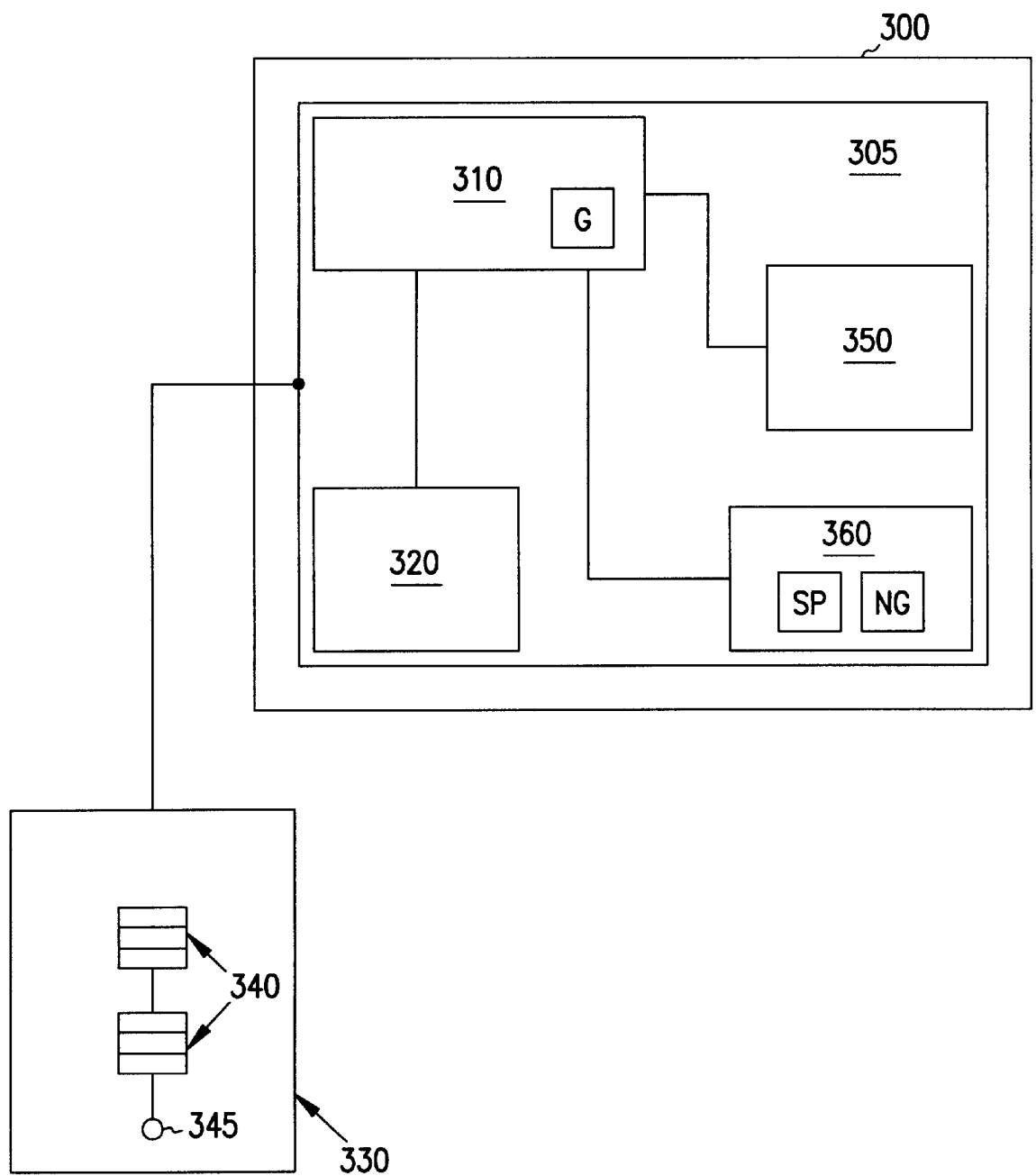
FIG. 3 is a drawing showing another embodiment of a functional diagram of an implantable medical device according to the teachings of the present invention.

FIG. 3 illustrates another embodiment of an automatic gain adjusting system 305 for shock lead system 330 as part of implantable medical device 300. Shown in FIG. 3 is automatic gain adjusting system 305 having sensing system 320, amplifier system 310, data storage 350 and threshold producer 360. In one embodiment, shock lead system 330 has shock leads 340. In another embodiment, shown in FIG. 3, shock lead system 330 has shock leads 340 and pacing lead 335. Amplifier 310 includes gain G. Threshold producer 360 includes scaling percentage SP and new gain NG. Shock lead system 330 is coupled to implantable medical device 300. Sensing system 320 is coupled to amplifier 310. Amplifier 310 is coupled to data storage 350. In one embodiment, amplifier 310 is a shock channel amplifier 310. Data storage 350 is coupled to threshold producer 360. In one embodiment, data storage 350 is a data collection register 350. Threshold producer 360 is coupled to amplifier 310. Automatic gain adjusting system 305 may be implemented in hardware, firmware, software, integrated circuits, modules or any combination of the above.

Automatic gain adjusting system 305, shown in FIG. 3, operates to automatically adjust the gain G for shock lead system 330 by first checking to see if the gain G was programmed after an initial delay. In one embodiment, the initial delay is 24 hours after shock lead system 330 was implanted. In another embodiment, the initial delay is 24 hours after taking implantable medical device 300 out of storage mode. Next, amplifier 310 is enabled, if not already enabled. Gain value G in amplifier 310 is then set to a predetermined initial gain (IG) level. In one embodiment, IG is a low value. In another embodiment, IG is a level that will facilitate generation of an R-wave that is above the noise level. R-waves and noise levels are known to those of skill in the art and, therefore, are not described here. Other embodiments for different IG levels for the present invention exist without departing from the scope of the present invention. Next, the output of amplifier 310 is allowed to stabilize for a period of time A. In one embodiment, period of time A is at least four seconds. After period of time A, data storage 350 is cleared. Data storage 350 then captures data from amplifier 310 for a period of time B. In one embodiment, period of time B is at least six seconds. Data storage 350 is then read by the threshold producer 360. Threshold producer 360 determines the maximum output value (M) recorded by data storage 350. New gain NG is then produced. In one embodiment, NG is produced using M, a predetermined range (R) of values, and predetermined scaling percentage SP. In one embodiment, R is a preset range of values going from a lower value, or minimum, such as 0, to an upper value, or maximum, such as 127, that can be used for properly operating implantable medical device 300. Scaling percentage SP represents the amount of R that is to be taken up by the maximum signal M. If M is equal to the upper value of available range R, the signal is clipping and gain value G is set to a minimum value, such as 0. If M is less than the upper value of R, new gain NG is produced by threshold producer 360 to scale the maximum signal to a desired level. In one embodiment, M is scaled using scaling percentage SP to fit the signal into the desired range. In one embodiment, scaling percentage SP is preset to a value between a minimum value and a maximum value. In another embodiment, scaling percentage SP is preset to a value between 0 and 100%. In yet another embodiment, scaling percentage SP is preset to approximately 50%. In one embodiment, scaling percentage SP may be changed from the preset value by using a programmer device. This change can be done by a physician or other person to change the gain G after determining that the automatic gain produced is not optimal. In one embodiment, NG is produced using the formula: NG=(SP*C*IG)/M. In one embodiment, C is a constant that is equal to the number of values in R, e.g. C is 128 when R is 0 to 127. NG is then used to set gain G so the maximum output of shock channel amplifier 310 reaches the level selected by the scaling percentage SP. Shock lead system 330 is now calibrated regardless of whether implanted medical device 300 was programmed manually upon insertion.

In one embodiment, gain G may be reprogrammed. If, during a subsequent check of implantable medical device 300, such as a follow-up visit to the physician, the output of shock lead system 330 is found to not be optimal it can be reprogrammed. Using a programmer, a new value SP' for scaling percentage SP is selected. In one embodiment, SP' is selected to optimize system efficacy and patient care. SP' is then entered into the programmer. The programmer then uses telemetry to transmit SP' to implantable medical device 300. Telemetry between a programmer and implantable medical device 300 is known in the art and is, therefore, not described here. The programmer also sends an instruction, via telemetry, to implantable medical device 300 that directs automatic gain adjusting system 305 to run the calibration process again using SP'. Since only SP', instead of electrogram data, has to be passed between implantable medical device 300 and the programmer via telemetry there is a significant reduction in the effect noise will have on reprogramming, thereby allowing for improved functionality of implantable medical device 300.

Figure 4:
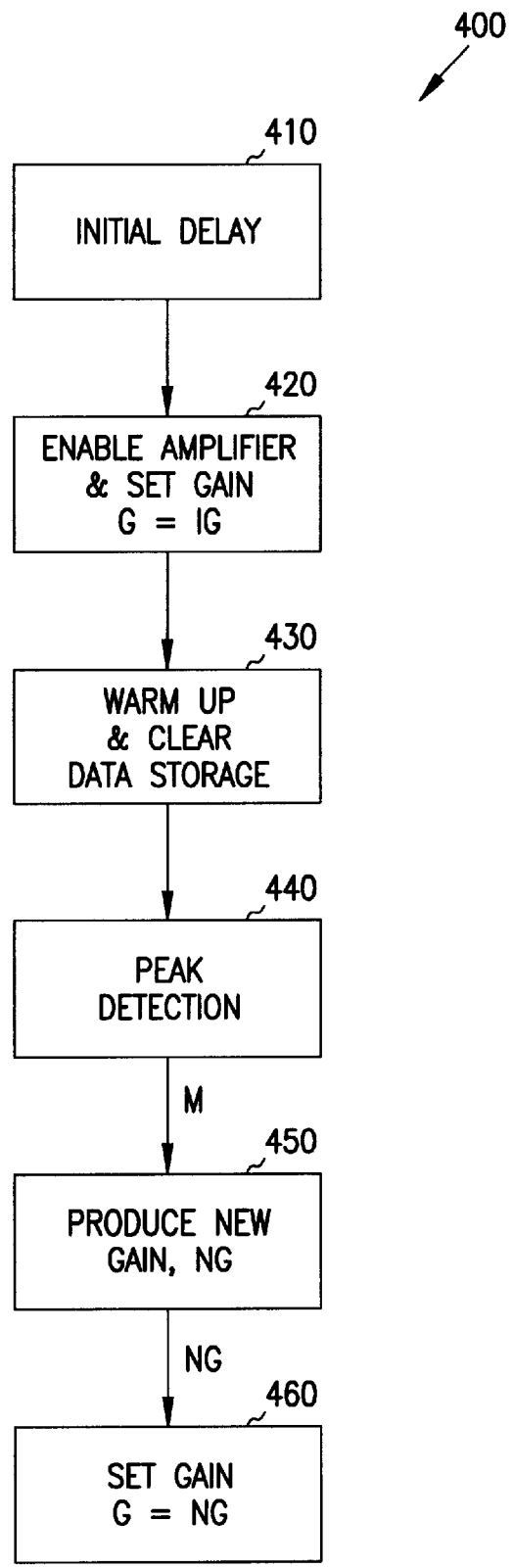
FIG. 4 is a block diagram of one embodiment of a method for automatically calibrating an implantable medical device according to the teachings of the present invention.

FIG. 4 illustrates a method 400 for automatically adjusting a shock lead system of an implantable medical device. The first step, shown in block 410, has the method 400 start only after an initial, or first, delay where calibrating did not occur during the initial delay. In one embodiment, the initial delay is set to 24 hours after implanting the implantable medical device. In another embodiment, the initial delay is set to 24 hours after the implantable medical device is taken out of storage mode. Next, shown in block 420, an amplifier, such as a shock channel amplifier, is enabled, if not already enabled. Additionally, a gain G for the amplifier is set to a predetermined initial gain IG. In one embodiment, IG is a low value. In another embodiment, IG is a level that will facilitate generation of an R-wave that is above the noise level. R-waves and noise levels are known to those of skill in the art and, therefore, are not described here. Next, shown in block 430, the amplifier is allowed to stabilize for a period of time A. In one embodiment, period of time A is at least four seconds. Additionally, a data storage, such as a data collection register, is cleared of all preceding values. After the period of time A, the output of the amplifier is captured into the data storage for a period of time B. In one embodiment, period of time B is at least six seconds. Next, the values in the data storage are analyzed to find the maximum value (M). A new gain NG is then produced, shown in block 450. In one embodiment, NG is produced using M, a predetermined range (R) of values, and predetermined scaling percentage SP. In one embodiment, R is a preset range of values going from a lower boundary, or minimum, such as 0, to an upper boundary, or maximum, such as 127, that can be used for properly operating implantable medical device. SP represents the amount of the range R that is to be taken up by maximum signal M. If M is equal to the upper boundary of R, the signal is clipping and NG is set to a value less than initial gain IG. In one embodiment, NG is set to a minimum value, such as 0. If M is less than the upper boundary of R, NG is produced to scale the maximum signal to a desired level. In one embodiment, NG is produced using scaling percentage SP. In one embodiment, SP is preset to a value between a minimum value and a maximum value. In another embodiment, SP is preset to a value between 0 and 100%. In yet another embodiment, SP is preset to approximately 50%. In one embodiment, scaling percentage SP may be changed from the preset value by using a programmer device. This change can be done by a physician or other person to change the gain G after determining that the automatic gain produced is not optimal. In one embodiment, NG is produced using the formula: NG=(SP*C*IG)/M. In one embodiment, C is a constant that is equal to the number of values in R, e.g. C is 128 when R is 0 to 127. Gain value G is then set to NG, shown in block 460, where the maximum output of the amplifier will now reach the level selected by the scaling percentage SP or any other desired preset level. Shock lead system 400 is now calibrated regardless of whether the implantable medical device was programmed manually upon insertion.

In one embodiment, gain G may be reprogrammed. If, during a subsequent check of the implantable medical device, such as a follow-up visit to the physician, the output of the shock lead system is found to not be optimal it can be reprogrammed. Using a programmer, a new value SP' for scaling percentage SP is selected. In one embodiment, the SP' is selected to optimize system efficacy and patient care. SP' is then entered into the programmer. The programmer then uses telemetry to transmit SP' to the implantable medical device. Telemetry between a programmer and an implantable medical device is known in the art and is, therefore, not described here. The programmer also sends an instruction, via telemetry, to the implantable medical device that directs implantable medical device to run the calibration process again using SP'. Since only SP', instead of electrogram data, has to be passed between the implantable medical device and the programmer via telemetry there is a significant reduction in the effects noise will have on reprogramming, thereby allowing for improved functionality of the implantable medical device.

Figure 5:
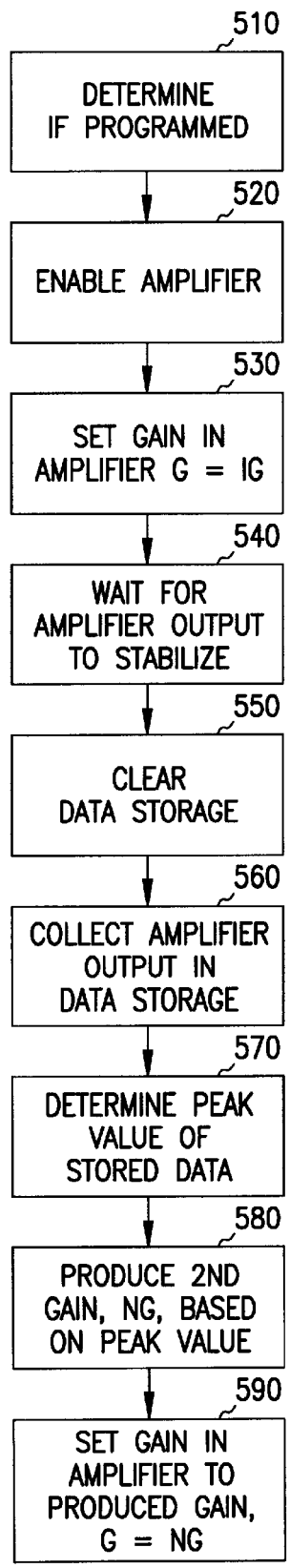
FIG. 5 is a block diagram of another embodiment of a method for automatically calibrating an implantable medical device according to the teachings of the present invention.

FIG. 5 illustrates another embodiment of a method for automatically calibrating the gain for a shock lead system in an implantable medical device. First, shown in block 510, it is determined if the implantable medical device has been programed with a period of time A. In one embodiment, A is at least 24 hours after the implantable medical device is implanted and taken out of storage mode. Next, shown in block 520, the amplifier for the shock lead system is enabled, if it is not already enabled. In one embodiment, the amplifier is a shock channel amplifier. Gain G for the shock lead system amplifier is then set, in block 530, to a predetermined initial gain IG. In one embodiment, IG is a low value. In another embodiment, IG is a level that will facilitate generation of an R-wave that is above the noise level. R-waves and noise levels are known to those of skill in the art and, therefore, are not described here. After setting IG, the amplifier output is allowed to stabilize for a period of time B, shown in block 540. In one embodiment, period of time B is at least six seconds. Next, shown in block 550, data storage is cleared. In one embodiment, data storage is a data collection register. After data storage is cleared, the output of the amplifier is collected in data storage, shown in block 560. Shown in block 570, a peak value is then determined for the stored data. Next, new gain NG is produced based on the peak value as shown in block 580. Finally, NG is used to set gain G in the amplifier. The shock lead system is now calibrated regardless of whether the implantable medical device was programmed manually upon implantation.

Figure 6A:
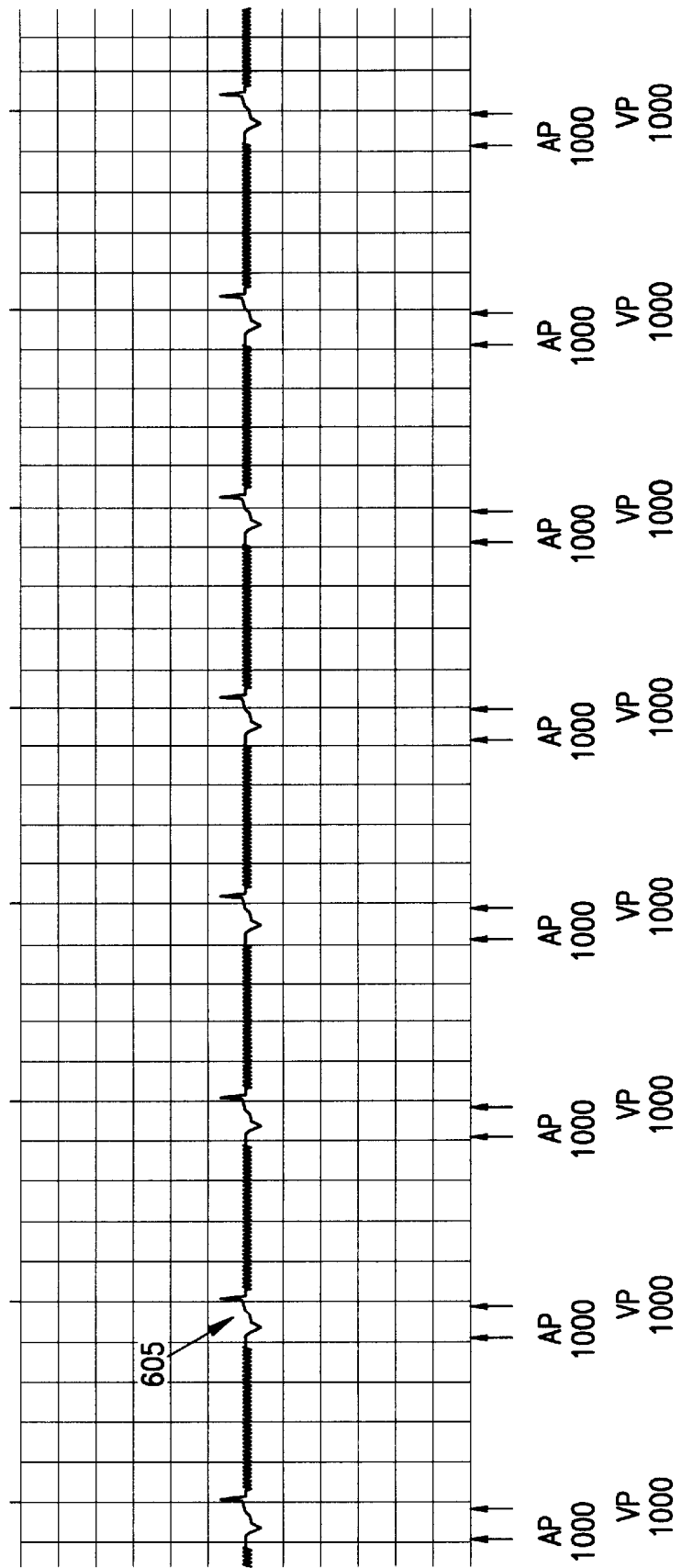
FIGS. 6A–6D are example output readings for an electrogram signal.
Figure 6B:
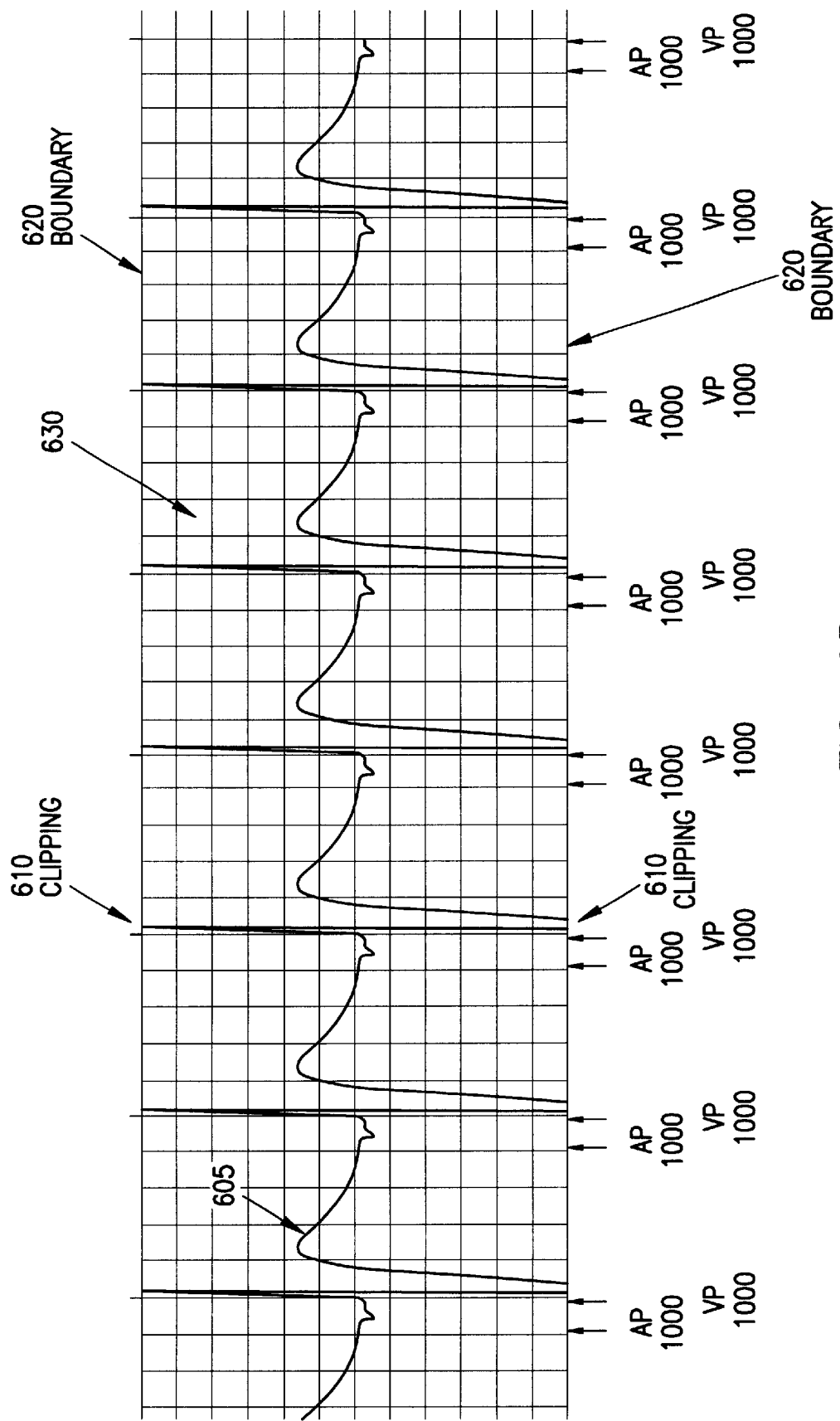
Figure 6C:
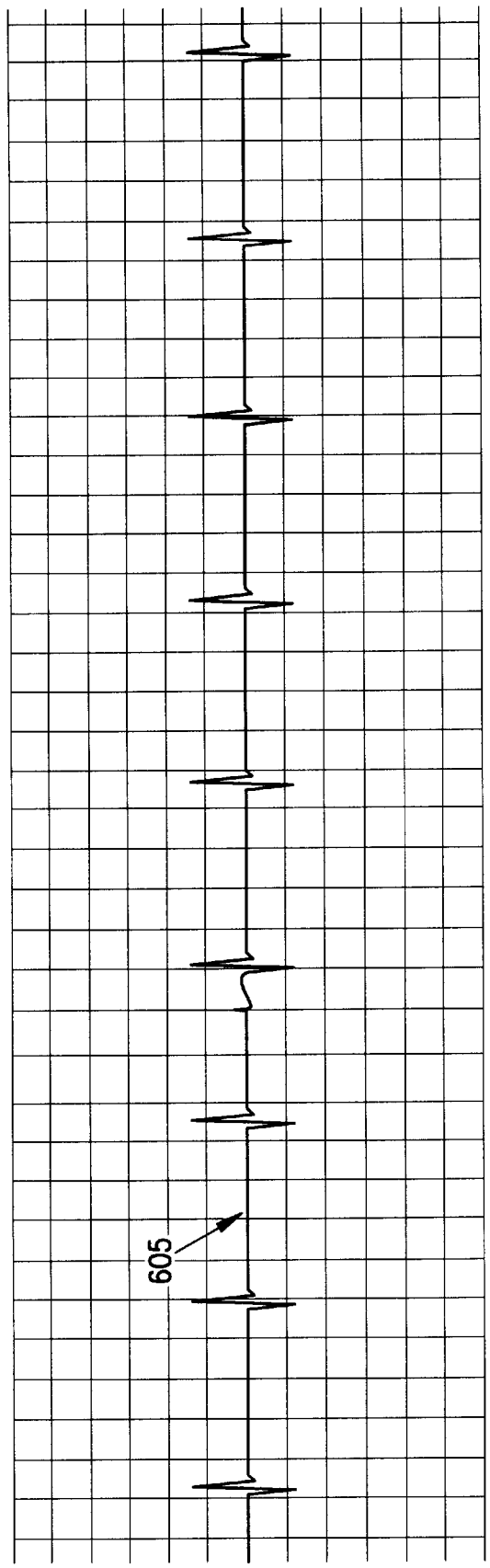
Figure 6D:
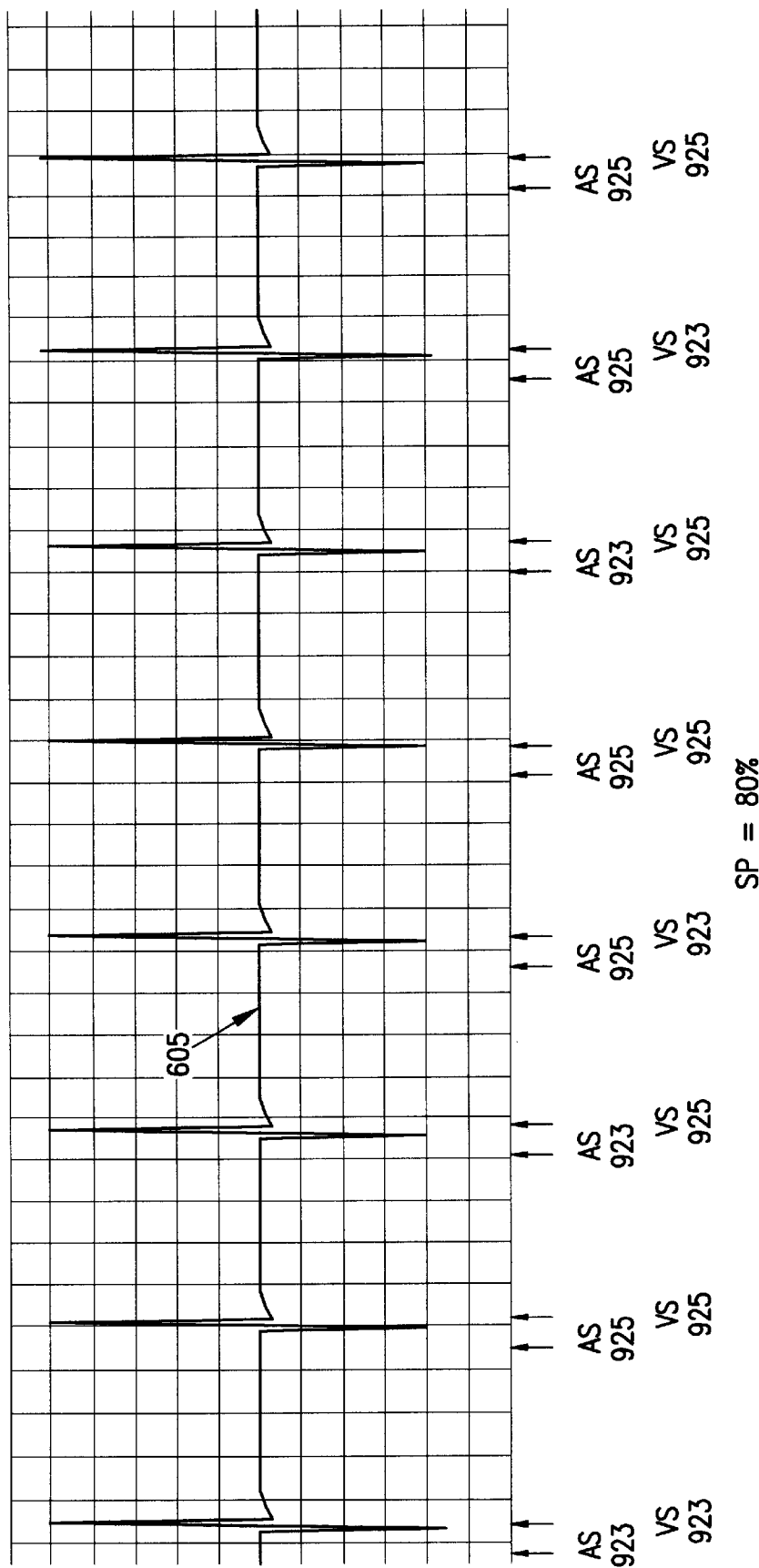

FIGS. 6A–6D illustrate many of the conditions described above for the output of an amplifier in an implantable medical device according to the teachings of the present invention. FIG. 6A illustrates a signal 605 where gain factor G in the amplifier is too low. When G is too low signal 605 is not distinguishable from noise included in signal 605 and the implantable medical device may record data that is not distinguishable from noise making it useless for therapeutic activities. FIG. 6B illustrates the converse problem where the gain factor G in the amplifier is too high. If G is too high, signal 605 will clip 610 at boundaries 620 of output region 630. Similar to when G is too low, the implanted medical device may record data that is not valid, also making it useless for therapuetic activities. FIG. 6C illustrates an output signal 605 operating with gain value G that has been scaled using scaling percentage SP set at 20% of the maximum. FIG. 6D illustrates output signal 605 operating with gain value G that has been scaled using scaling percentage SP set at 80% of the maximum. Both FIGS. 6C and 6D have output signal 605 that is operating in a valid state where signal 605 is distinguishable from noise and is not clipping, thereby allowing for the implantable medical device to operate properly.

Thus, a method and apparatus for automatic shock lead calibration has been shown. The system automatically sets the gain of the shock lead system to a value that will ensure a predetermined amount of the available range of values is used. With the value in this range, the implantable medical device, that the shock lead system is part of, is more likely to operate properly even if the physician who implanted the device forgot to program it. Additionally, with calibration abilities in the implantable medical device, the implantable medical device can be reprogrammed with fewer effects from noise.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof

What is claimed is:

1. An implantable medical device comprising:

a storage location for storing and setting a gain in a storage mode and a nonstorage mode;

a shock lead system including at least one shock lead;

an automatic gain adjusting system, coupled to the shock lead system, which includes;

a detector, communicatively coupled to the storage location, which detects that the gain value for the shock lead system was not set on exiting the storage mode; and a gain determining module, communicatively coupled to the detector and the storage location, which produces and stores a new gain value upon detection of the gain value not being set on exiting the storage mode.

2. The implantable medical device of claim 1, wherein the gain determining module comprises:

a sensing system coupled to the shock lead system;

an amplifier coupled to the sensing system;

a data storage device coupled to the amplifier; and a threshold producer coupled to the data storage device and the amplifier.

3. The implantable medical device of claim 2, wherein the amplifier is a shock channel amplifier.

4. The implantable medical device of claim 2, wherein the data storage device is a data register.

5. The implantable medical device of claim 1, wherein the implantable medical device is an implantable pacing/defibrillation device.

6. The implantable medical device of claim 1, wherein the implantable medical device is an implantable defibrillator.

7. The implantable medical device of claim 1, wherein the shock lead system further comprises at least one pacing lead.

* * * * *